US009221893B2

(12) United States Patent
Hahn et al.

(10) Patent No.: US 9,221,893 B2
(45) Date of Patent: Dec. 29, 2015

(54) HYALURONIC ACID-PROTEIN CONJUGATES AND METHOD FOR PREPARING SAME

(75) Inventors: Sei Kwang Hahn, Pohang-si (KR); Jeong A. Yang, Pohang-si (KR); Seung Kyu Yoon, Seocho-gu (KR); Won Hee Hur, Seocho-gu (KR); Ki Tae Park, Jeonju-si (KR); Hye Min Kim, Pohang-si (KR); Hyun Tae Jung, Pohang-si (KR)

(73) Assignee: POSTECH ACADEMY-INDUSTRY FOUNDATION, Pohang-si, Gyeongsangbuk-do (KR)

(*) Notice: Subject to any disclaimer, the term of this patent is extended or adjusted under 35 U.S.C. 154(b) by 0 days.

(21) Appl. No.: 13/992,988

(22) PCT Filed: Dec. 5, 2011

(86) PCT No.: PCT/KR2011/009363
§ 371 (c)(1),
(2), (4) Date: Jun. 10, 2013

(87) PCT Pub. No.: WO2012/077950
PCT Pub. Date: Jun. 14, 2012

(65) Prior Publication Data
US 2013/0253170 A1 Sep. 26, 2013

(30) Foreign Application Priority Data
Dec. 10, 2010 (KR) .......................... 10-2010-0126432

(51) Int. Cl.
| | | |
|---|---|---|
| *C07K 14/56* | (2006.01) | |
| *C07K 14/565* | (2006.01) | |
| *C07K 14/57* | (2006.01) | |
| *C07K 14/525* | (2006.01) | |
| *C07K 17/10* | (2006.01) | |
| *A61K 38/21* | (2006.01) | |
| *A61K 47/48* | (2006.01) | |
| *A61K 31/726* | (2006.01) | |
| *A61K 31/728* | (2006.01) | |
| *A61K 47/36* | (2006.01) | |
| *A61K 38/19* | (2006.01) | |

(52) U.S. Cl.
CPC .............. *C07K 14/56* (2013.01); *A61K 31/726* (2013.01); *A61K 31/728* (2013.01); *A61K 38/191* (2013.01); *A61K 38/21* (2013.01); *A61K 38/212* (2013.01); *A61K 38/215* (2013.01); *A61K 38/217* (2013.01); *A61K 47/36* (2013.01); *A61K 47/4823* (2013.01); *C07K 14/525* (2013.01); *C07K 14/565* (2013.01); *C07K 14/57* (2013.01); *C07K 17/10* (2013.01)

(58) Field of Classification Search
CPC .. C07K 14/56; C07K 14/565; A61K 47/4823; A61K 31/726; A61K 31/728; A61K 31/21; A61K 38/215
See application file for complete search history.

(56) References Cited

U.S. PATENT DOCUMENTS

| | | | | |
|---|---|---|---|---|
| 5,677,276 A | * | 10/1997 | Dickerson et al. | 514/9.4 |
| 2004/0126361 A1 | | 7/2004 | Saifer et al. | |
| 2004/0136952 A1 | | 7/2004 | Bhaskaran et al. | |
| 2005/0176108 A1 | * | 8/2005 | Kim et al. | 435/70.21 |
| 2009/0082266 A1 | * | 3/2009 | Nakamura et al. | 514/12 |

FOREIGN PATENT DOCUMENTS

| | | |
|---|---|---|
| EP | 1579873 A1 | 9/2005 |
| JP | 2008-525491 A | 7/2008 |

OTHER PUBLICATIONS

Yang, J-A. et al. Target specfic hyaluronic acid-interferon alpha conjugate for the treatment of hepatitis C virus infection. Biomaterials, 2011, vol. 32, p. 8722-8729.*
Bouhadir K.H. et al. Synthesis of cross-linked poly(aldehyde guluronate) hydrogels. Polymer, 1999, vol. 40, p. 3575-3584.*
Matthews, S. J. et al. Peginterferon alfa-2a: A review of approved and investigational uses. Clinical Therapeutics, 2004, vol. 26, No. 7, p. 991-1025).*
Office Action issued Aug. 1, 2014 in CN Application No. 201180067381.X.
Oh et al, "Target specific and long-acting delivery of protein, peptide, and nucleotide therapeutics using hyaluronic acid derivatives," Journal of Controlled Release, vol. 141, pp. 2-12 (2010).
Office Action issued Jun. 20, 2014 in CA Application No. 2,821,075.
Int'l Search Report issued Jun. 15, 2012 in Int'l Application No. PCT/KR2011/009363.
Office Action issued Oct. 14, 2014 in JP Application No. 2013-543093.

* cited by examiner

*Primary Examiner* — Robert Landsman
*Assistant Examiner* — Bruce D Hissong
(74) *Attorney, Agent, or Firm* — Panitch Schwarze Belisario & Nadel LLP

(57) ABSTRACT

An HA-protein conjugate in which an HA-aldehyde derivative, in which an aldehyde group is introduced to a hyaluronic acid or a salt thereof, is conjugated to the N-terminus of a protein, and a method for preparing the same are provided. The HA-protein conjugate includes a protein drug exhibiting an excellent bioconjugation efficiency and long-term medicinal effects, and has excellent protein drug activities since the hyaluronic acid is specifically conjugated to the N-terminus of the protein. Also, since liver-targeting properties of the hyaluronic acid can be freely controlled by changing an aldehyde substitution rate of the HA-aldehyde derivative, the HA-protein conjugate can be effectively used as a protein drug for treating liver diseases, and also be useful in enabling long-term medicinal effects of a protein drug required to bypass the liver. Accordingly, the HA-protein conjugate can be effectively used for a drug delivery system of proteins.

20 Claims, 6 Drawing Sheets

A    B

HYALURONIC ACID-PROTEIN CONJUGATES AND METHOD FOR PREPARING SAME

CROSS-REFERENCE TO RELATED APPLICATION

This application is a Section 371 of International Application No. PCT/KR2011/009363, filed Dec. 5, 2011, which was published in the Korean language on Jun. 14, 2012, under International Publication No. WO 2012/077950 A3, and the disclosure of which is incorporated herein by reference.

TECHNICAL FIELD

The present invention relates to a hyaluronic acid-protein conjugate and a method for preparing the same.

BACKGROUND ART

Studies on formulations in which medicinal effects of a protein drug last for a long period of time have been mainly conducted to develop formulations through a conjugation reaction with a biocompatible biodegradable polymer. The time for which the medicinal effect of the above-described protein drug lasts extends to several weeks according to the shape of a formulation, and an effective medical ingredient to be conjugated. To develop such a formulation, biocompatibility of a polymer which is conjugated with the effective medical ingredient should be considered in addition to maintenance of the medicinal effects of the formulation and an increase in the time for which the medicinal effect lasts. Also, problems such as a decrease in activity of the protein drug caused by conjugation with the polymer should be taken into consideration.

By way of example of the studies on such a formulation, active research to apply to the drug delivery system by conjugating an effective medical ingredient with biocompatible biodegradable polyethylene glycol (PEG) or hyaluronic acid (HA) has been conducted so far.

However, PEG used for a reaction for conjugating PEG with an effective medical ingredient, that is, a PEGylation reaction, is one of representative polymer materials for living organisms approved by the Food and Drug Administration (FDA), but an 'accelerated blood clearance (ABC)' phenomenon in which a drug administered into the body disappears more rapidly when a PEG-liposome conjugate used as a drug delivery carrier is repeatedly injected was reported to take place. In the case of interferon alpha (IFNα), which is a protein drug for treating liver diseases, a PEGylated product is actually produced into a once-a-week injection formulation. A PEGylated interferon drug for treating hepatitis C exhibits severe side effects, and thus there are many cases of patients discontinuing their treatment. Also, the interferon drug shows an anti-viral effect of only approximately 50% in patients with CV genotype 1. Therefore, development of new drugs is required. A drug delivery carrier using PEG serves to simply increase a body retention time without exhibiting delivery characteristics into certain tissues, and thus requires a targeting moiety to deliver it into a certain tissue to treat a certain disease.

Meanwhile, when HA is conjugated with an effective medical ingredient, the resulting conjugate may be specifically delivered to tissues of the liver. However, bioconjugation efficiency by the conjugation reaction between the HA and the effective medical ingredient is low, and thus a limit to the bioconjugation efficiency has been shown.

Also, when the polymer such as PEG or HA is conjugated with the protein drug, the polymer may non-specifically react with various reactive groups in an amino acid sequence of a protein to destroy a tertiary structure of the protein, thereby degrading bioactivities of the protein drug.

DISCLOSURE

Technical Problem

The present invention is directed to providing a method for preparing a hyaluronic acid (HA)-protein conjugate capable of exhibiting high bioconjugation efficiency while maintaining bioactivities of a protein drug to the maximum and being applicable to various water-soluble effective medical ingredients, an HA-protein conjugate prepared by the method, and use of the HA-protein conjugate.

Technical Solution

One aspect of the present invention provides a method for preparing an HA-protein conjugate. The method includes allowing an HA-aldehyde derivative in which an aldehyde group is introduced into HA or a salt thereof to react with the N-terminus of a protein.

Another aspect of the present invention provides an HA-protein conjugate in which an HA-aldehyde derivative in which an aldehyde group is introduced into HA or a salt thereof is conjugated to the N-terminus of a protein.

Hereinafter, the HA-protein conjugate and the method for preparing the same according to exemplary embodiments the present invention will be described in further detail.

HA is a high molecular weight linear polysaccharide including a disaccharide, in which D-glucuronic acid (GlcA) and N-acetyl-D-glucosamine (GlcNAc) are bound via a β1,3-glycosidic bond, as a repeating unit. The disaccharide repeating unit of the HA is represented by the following Formula 1.

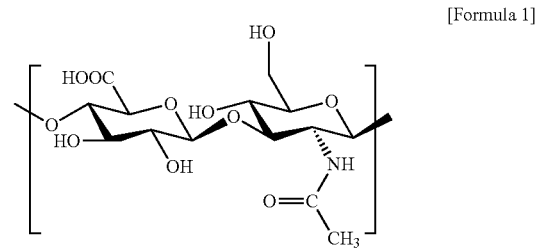

[Formula 1]

According to the present invention, the term "hyaluronic acid" or (HA) is interpreted to include HA including the disaccharide of Formula 1 as a repeating unit and also a derivative of the HA including a derivative derived from the disaccharide backbone of Formula 1 as a repeating unit. The derivative of the HA refers to HA having a structure in which a carboxyl group, a hydroxyl group, an acetyl group, or the terminus of the disaccharide repeating unit in the disaccharide structure of Formula 1 is substituted with another substituent. For example, the substituent may be, for example, at least one substituent selected from the group consisting of hydrogen, a C1-6 alkyl group, a C1-6 alkylcarbonyl group, a carboxyl group, a hydroxyl group, and an acetyl group.

A hyaluronate includes salts of the HA or a derivative thereof. For example, the hyaluronate may include a sodium salt, a potassium salt, a magnesium salt, a calcium salt, an aluminum salt, etc., but the present invention is not limited thereto.

The present invention is directed to providing a method for preparing an HA-protein conjugate, which includes allowing an HA-aldehyde derivative in which an aldehyde group is introduced into HA or a salt thereof to react with the N-terminus of a protein.

As the method of conjugating HA with a protein, a method of binding an amine group of a protein to a carboxyl group of HA has been used in the related art. However, such a method has problems in that a reaction is complicated and efficiency of the reaction, that is, bioconjugation efficiency, may be degraded since a linker is generally used to form a bond between the amine group of the protein and the carboxyl group of the HA, and the carboxyl group of the HA may non-specifically react with an amine group of lysine which is present in plural number in the amino acid sequence of the protein as well as the N-terminus of the protein.

Meanwhile, in the present invention, bioconjugation efficiency and reaction specificity in an HA-protein conjugation reaction may be significantly improved using the HA-aldehyde derivative instead of the carboxyl group of the HA.

The term "HA-aldehyde derivative" used in the present invention is interpreted to include all derivatives of the HA or salt thereof into which an aldehyde group is introduced.

According to one exemplary embodiment, the HA-aldehyde derivative may be a derivative in which at least one aldehyde group is introduced into the glucuronic acid backbone of the HA or salt thereof.

The HA-aldehyde derivative according to the present invention includes an aldehyde group at the glucuronic acid backbone of the HA or salt thereof. Therefore, a substitution rate of the aldehyde group may be easily controlled, compared with use of the HA-aldehyde derivative in which an aldehyde group is formed at the terminus of the disaccharide repeating unit of the HA. According to one exemplary embodiment of the present invention, the expression "substitution rate of an aldehyde group" means that a certain functional group of HA or a salt thereof is replaced or modified with an aldehyde group. The substitution rate with the aldehyde group is defined as a ratio of repeating units substituted with aldehyde groups in a total of the HA repeating units. By definition, the substitution rate may be expressed as a value greater than 0 and 1 or less, or greater than 0% and 100% or less, or a value greater than 0 mol % and 100 mol % or less. Since the substitution rate of the aldehyde group may be controlled to determine whether the HA-aldehyde derivative targets or bypasses the liver, the aldehyde group has an advantage in that targetability to the liver may be controlled according the kind of drug conjugated with HA.

According to one exemplary embodiment, the HA-aldehyde derivative may be a derivative having at least one aldehyde group at the terminus of a ring which is opened at the glucuronic acid backbone of the HA or salt thereof. For example, such an HA-aldehyde derivative includes a polymer containing at least one repeating unit represented by the following Formula 2.

[Formula 2]

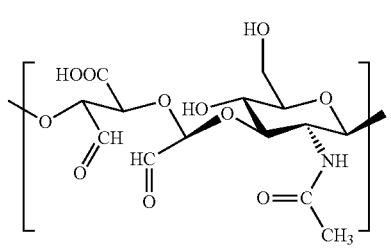

A method of preparing such an HA-aldehyde derivative is not particularly limited. For example, the glucuronic acid may be ring-opened, and at least one aldehyde group may be formed at the terminus of the opened ring using a known method, as apparent to those skilled in the related art.

According to one exemplary embodiment, the HA-aldehyde derivative containing at least one aldehyde group at the terminus of the ring which is opened at the glucuronic acid backbone of the HA or salt thereof may be obtained by allowing the HA or salt thereof to react with an oxidizing agent. One example of a method of forming the HA-aldehyde derivative is schematically shown in the following Scheme 1.

[Scheme 1]

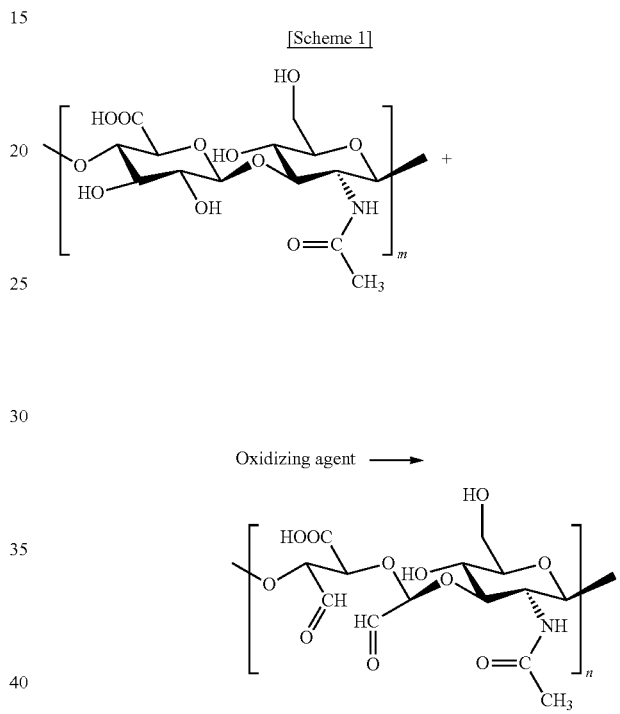

In the schemes disclosed in this specification, m and n represent the numbers of repetitions of the repeating unit. Here, m and n may be each independently an integer ranging from 1 to 10,000.

As shown in Scheme 1, some repeating units in the HA or salt thereof may be derived from the structure represented by Formula 2.

According to one exemplary embodiment, the oxidizing agent may induce a ring-opening reaction of glucuronic acid. For example, the oxidizing agent may include a periodate, for example, sodium periodate, potassium periodate, etc., but the present invention is not limited thereto. When the periodate is used as the oxidizing agent, the HA derivative having a substitution rate of 10% may be obtained by allowing the HA or salt thereof to react with the periodate for 2 hours in a dark place. Also, the HA derivative having a substitution rate of 50% may be obtained by allowing the HA or salt thereof to react with the periodate for 24 hours in a dark place. The aldehyde substitution rate of the HA can be controlled by controlling a time required for a reaction with the oxidizing agent. In this case, the aldehyde substitution rate may be properly selected and controlled according to the kind of the protein drug to be conjugated with the HA, as apparent to those skilled in the related art.

According to another exemplary embodiment of the present invention, the HA-aldehyde derivative may be a derivative in which an aldehyde group is introduced at a carboxyl position present at the glucuronic acid backbone of the HA or salt thereof. Methods of introducing an aldehyde group at a carboxyl position of HA may be widely selected by those skilled in the related art. For example, such an HA-aldehyde derivative includes a polymer containing at least one repeating unit represented by the following Formula 3, but the present invention is not limited thereto.

[Formula 3]

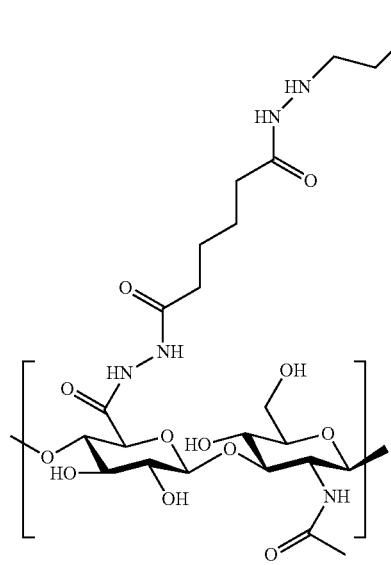

A method of preparing such an HA-aldehyde derivative is not particularly limited. For example, the aldehyde group may be introduced at the carboxyl position present at the glucuronic acid backbone of the HA or salt thereof using a known method, as apparent to those skilled in the related art.

According to one exemplary embodiment, the HA-aldehyde derivative in which the aldehyde group is introduced at the carboxyl position present at the glucuronic acid backbone of the HA or salt thereof may be obtained by allowing a carboxyl group of HA or a derivative thereof to react with a molecule containing a diamine or dihydrazide group, followed by allowing a derivative of the molecule to react with another molecule containing a dialdehyde group. One example of a method of forming the HA-aldehyde derivative is schematically shown in the following Scheme 2.

[Scheme 2]

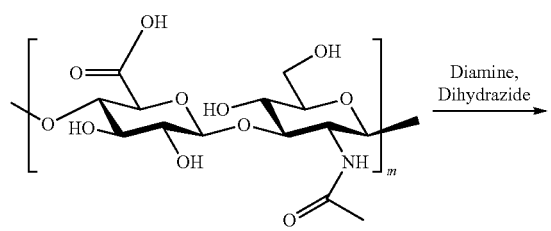

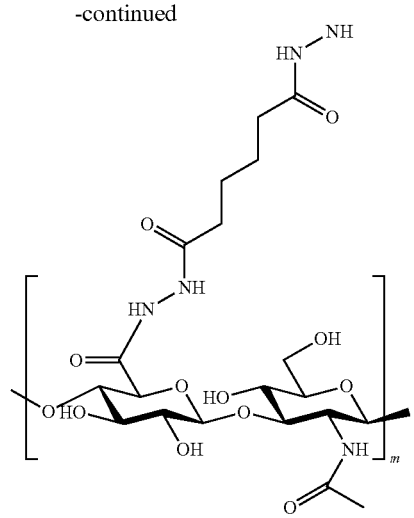

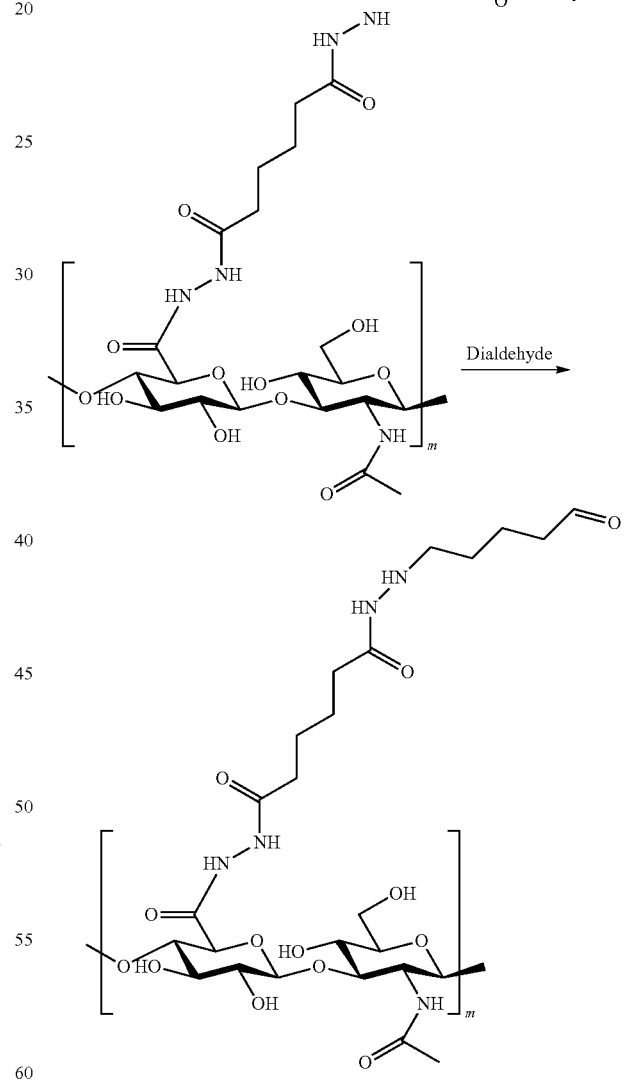

As shown in Scheme 2, an HA derivative having a hydrazide or amine group may be synthesized by allowing carboxyl groups of some repeating units in the HA or salt thereof to react with a molecule having a hydrazide group or an amine group at the terminus thereof, and an HA derivative having an aldehyde group introduced thereinto may be synthesized by allowing the HA derivative to react with a molecule having aldehyde groups at both termini thereof. The molecule having hydrazide or amine groups at both termini thereof is not particularly limited. For example, the molecule having the hydrazide or amine groups at both termini thereof may include adipic acid dihydrazide (ADH), hexane dihydrazide, heptane dihydrazide, octane dihydrazide, nonane-1,9-diamine, octane-1,8-diamine, hexamethlyene diamine (HMDA), diaminopentane, diaminobutane, diaminoethane, etc. The molecule having aldehyde groups introduced at both termini thereof is not particularly limited. For example, the molecule having the aldehyde groups introduced at both termini thereof may include adipaldehyde, heptanedial, octanedial, glutaraldehyde, etc. When a derivative is synthesized using ADH, an HA derivative in which 20% or 70% of ADH is substituted, respectively, may be obtained when a reaction is performed for 3 minutes or 2 hours. When a derivative is synthesized using an HA-ADH derivative and glutaraldehyde, an HA-aldehyde derivative in which 20% or 70% of the HA-ADH derivative and glutaraldehyde are substituted may be obtained. Meanwhile, when the HA-aldehyde derivative according to the present invention is used, the aldehyde substitution rate of the HA-aldehyde derivative group may be controlled to determine whether the HA-aldehyde derivative targets or bypasses the liver, depending on the kind of a protein drug to be conjugated with HA.

The aldehyde substitution rate of the HA-aldehyde derivative according to one exemplary embodiment of the present invention may be freely controlled, for example, by controlling a treatment time of the oxidizing agent serving to induce a ring-opening reaction of glucuronic acid. Also, the substitution rate of the carboxyl group may be freely controlled by controlling a reaction time with the molecule having both the dihydrazide or diamine group and the carboxyl group of the HA.

According to one exemplary embodiment of the present invention, the HA-aldehyde derivative may have an aldehyde substitution rate of 5% or more and less than 30%. A protein conjugated with the HA-aldehyde derivative having an aldehyde substitution rate of 5% or more and less than 30% may target the liver.

According to one exemplary embodiment of the present invention, the HA-aldehyde derivative may have an aldehyde substitution rate of 30% or more and 100% or less. A protein conjugated with the HA-aldehyde derivative having an aldehyde substitution rate of 30% or more and 100% or less has target non-specific characteristics without targeting the liver.

In the following exemplary embodiments, it could be seen that the body retention time is short but the delivery characteristics into the liver are good when the HA-aldehyde derivative substituted at a low substitution rate of 10% is used, whereas the body retention time is increased more but the delivery characteristics into the liver are degraded when the HA-aldehyde derivative substituted at a low substitution rate of 45% is used.

The HA-protein conjugate according to the present invention may be prepared by binding the HA-aldehyde derivative prepared thus with the N-terminus of the protein.

The HA-protein conjugate according to the present invention may be, for example, a conjugate including at least one repeating unit represented by the following Formula 4 in the HA.

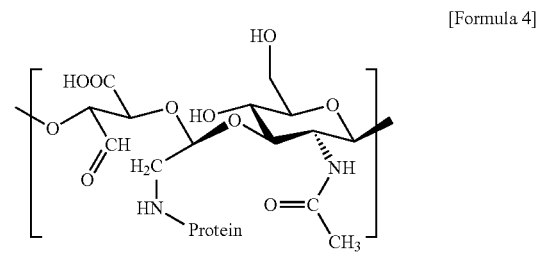

[Formula 4]

For example, when the HA-aldehyde derivative including at least one repeating unit of Formula 2 is conjugated with a protein, an amine group of the N-terminus of the protein reacts with the aldehyde group present in Formula 2 to form a conjugate, as seen from the following Scheme 3.

[Scheme 3]

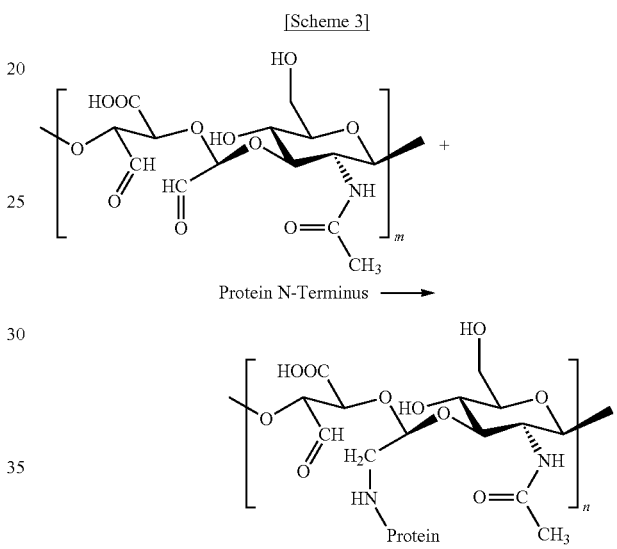

According to another exemplary embodiment, the HA-protein conjugate of the present invention may be, for example, a conjugate including at least one repeating unit represented by the following Formula 5 in the HA.

[Formula 5]

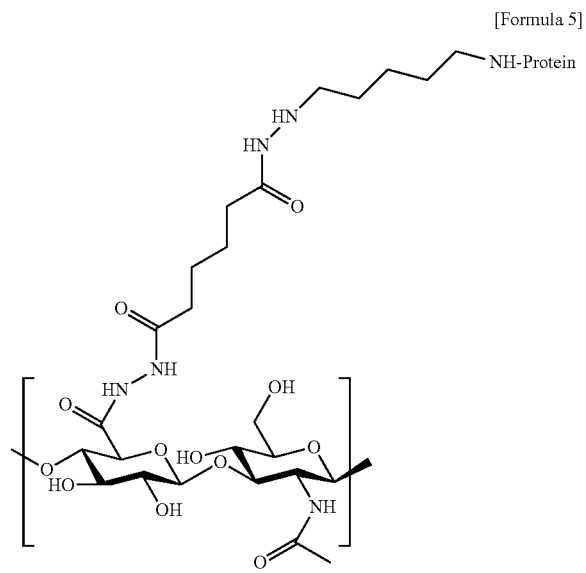

For example, when the HA-aldehyde derivative including at least one repeating unit of Formula 3 is conjugated with a protein, an amine group of the N-terminus of the protein reacts with the aldehyde group present in Formula 3 to form a conjugate, as seen from the following Scheme 4.

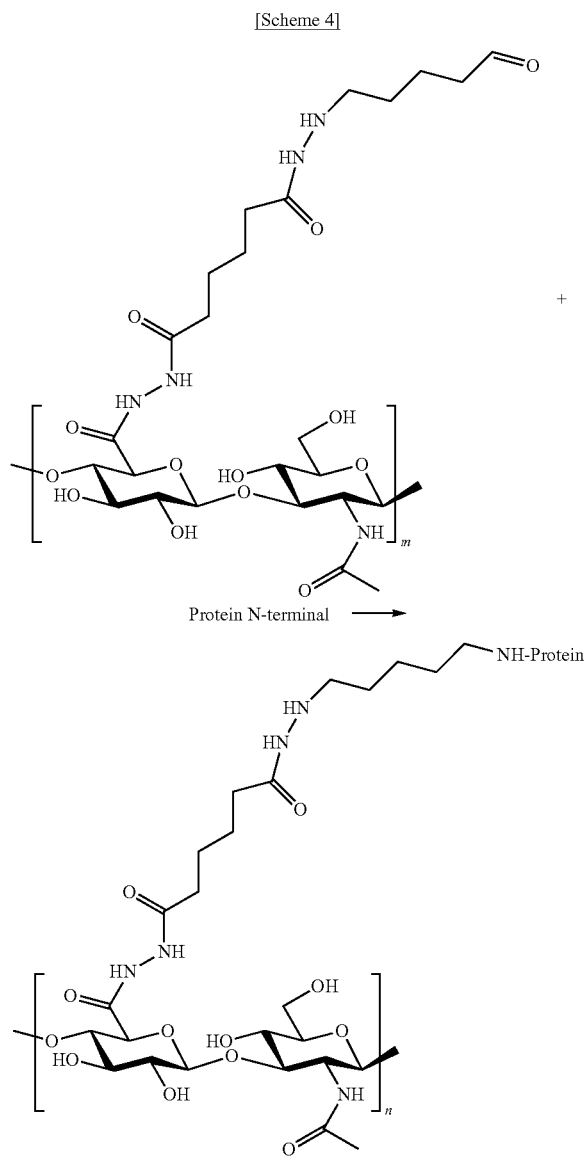

[Scheme 4]

The conjugation of the HA-aldehyde derivative with the protein may be preferably performed in the presence of a reagent serving to induce reductive amination. For example, when a direct reductive amination reagent such as sodium cyanoborohydride (NaBH$_3$CN) or sodium triacetoxyborohydride (NaBH(OCOCH$_3$)$_3$) is used, an HA-protein conjugation may be induced within a short time in a one-step manner.

Reaction of the HA-aldehyde derivative with the protein may be performed in a buffer solution with pH 5 to 7. It is preferred to control the pH value of the buffer solution within this pH range. This is because the aldehyde group of the HA-aldehyde derivative may be allowed to specifically react with the N-terminus of the protein without reacting with an amino acid of the protein such as lysine containing another amine group. More preferably, the reaction of the HA-aldehyde derivative with the N-terminus of the protein may be performed in a buffer solution with pH 5.5 to 6.5, and most preferably pH 6.0.

Meanwhile, an unreacted aldehyde group of the HA-aldehyde derivative which does not react with the N-terminus of the protein may be blocked with a protecting group. The unreacted aldehyde group of the HA-aldehyde derivative may be desirably blocked in advance since there is a probability of the unreacted aldehyde group unnecessarily reacting with another amino acid residue of a protein drug or another protein substance in the body during a process of preparing a drug delivery carrier or an in vivo administration process.

An alkyl carbazate such as ethyl carbazate or tetrabutyl carbazate, or an amino alcohol such as amino ethanol may be used as a material used to block the unreacted aldehyde group, but the present invention is not limited thereto. In general, it is possible to use an acylal protecting group, an acetal protecting group, and a ketal protecting group, which are known as protecting groups of the aldehyde group.

A method of blocking the unreacted aldehyde group as described above may be performed as shown in the following Scheme 5 or 6, but the present invention is not limited thereto.

[Scheme 5]

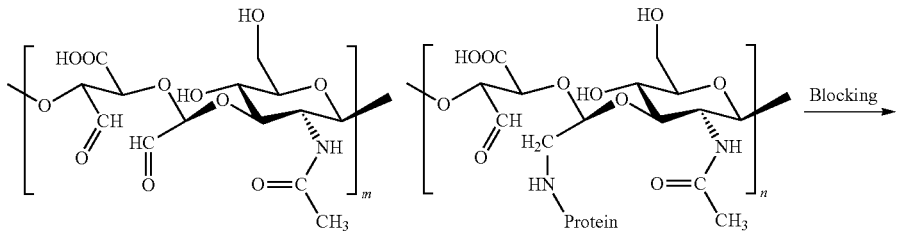

-continued

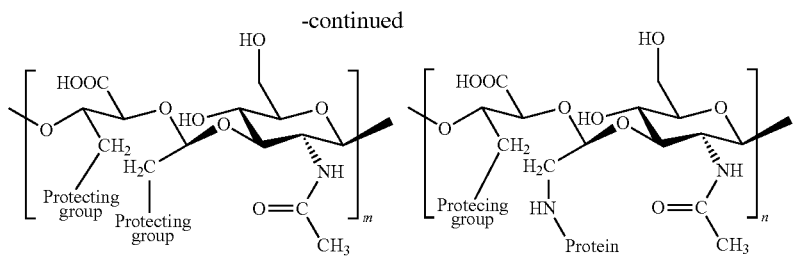

[Scheme 6]

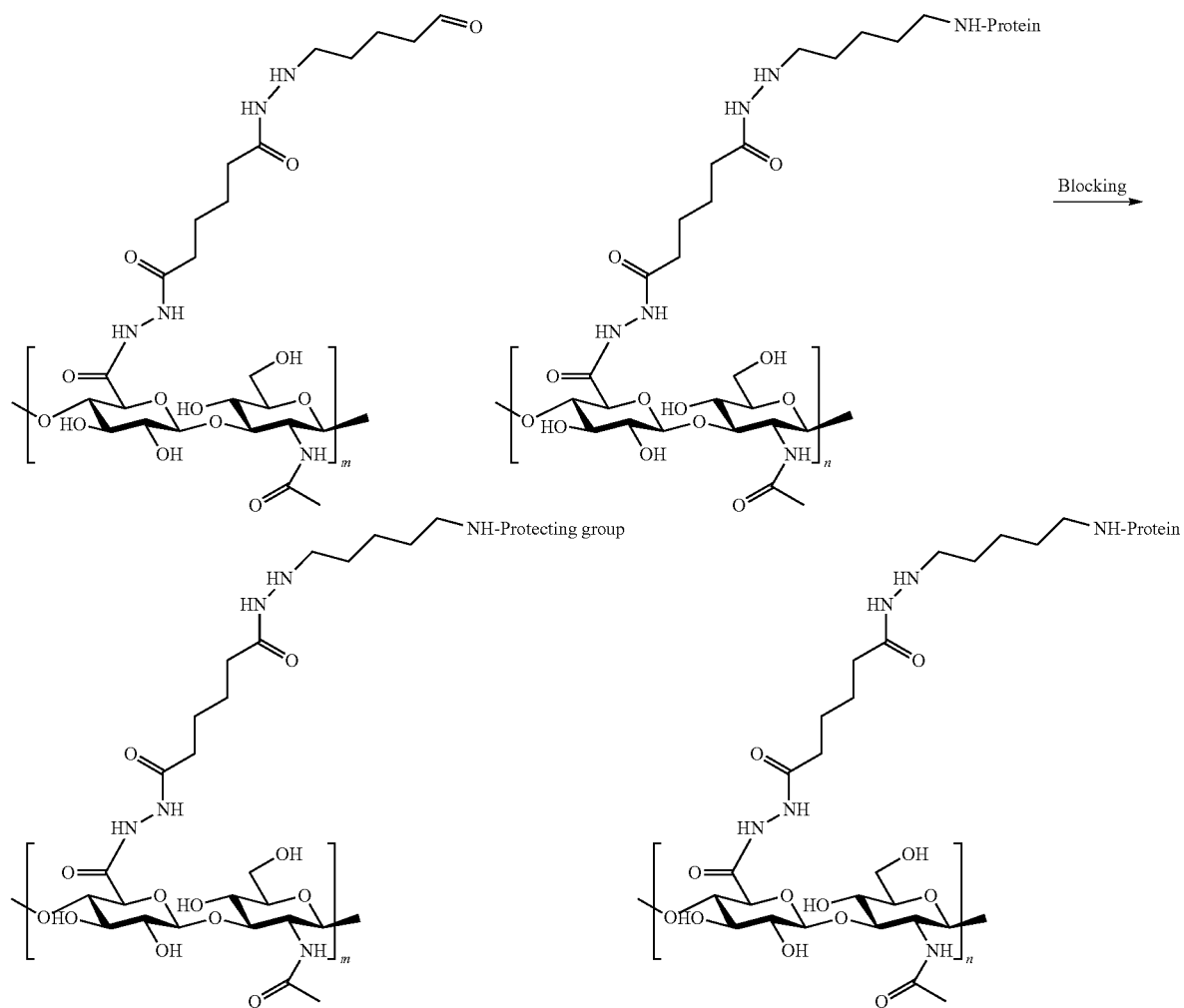

In the present invention, the HA or salt thereof used for preparation of the HA-protein conjugate may have a molecular weight of 10,000 to 3,000,000 daltons (Da), but the present invention is not limited thereto. The HA or salt thereof having this molecular weight may be effectively used to prepare a drug delivery carrier for sustaining a medicinal effect of a drug.

Meanwhile, the number of molecules of a protein conjugated per one molecule of the HA-aldehyde derivative may be controlled according to a concentration of an aqueous protein solution allowed to react with the HA-aldehyde derivative.

According to one exemplary embodiment, the protein in the HA-protein conjugate of the present invention may have 1 to 20 molecules bound per one molecule of the HA-aldehyde derivative. The HA-protein conjugate having a molecule number of the protein bound within this range may have a medicinal effect that lasts for a desired time, and may be applied as a therapeutic agent for treating liver disease due to good delivery characteristics into liver tissues.

The kind of protein drugs used for preparation of the HA-protein conjugate of the present invention is not particularly limited. The protein drug may be soluble in water so as to be easily applicable to the method according to the present invention, but the present invention is not limited thereto. Any kinds of protein drugs may be produced and used in the form of the HA-protein conjugate according to the present invention so as to ensure persistent medicinal effects of the proteins for a long period of time.

According to one exemplary embodiment, the protein may be interferon alpha (IFNα), interferon beta (IFNβ), interferon gamma (IFNγ), insulin, insulin-like growth factor 1 (IGF-1), growth hormone, erythropoietin, granulocyte-colony stimulating factors (GCSFs), granulocyte/macrophage-colony stimulating factors (GM-CSFs), interleukin-1 alpha, interleukin-1 beta, interleukin-3, interleukin-4, interleukin-6, interleukin-2, epidermal growth factors (EGFs), calcitonin, an adrenocorticotropic hormone (ACTH), a tumor necrosis factor (TNF), atobisban, buserelin, cetrorelix, deslorelin, desmopressin, dynorphin A (1-13), elcatonin, eleidosin, eptifibatide, growth hormone releasing hormone-II (GHRHII), gonadorelin, goserelin, histrelin, leuprorelin, lypressin, octreotide, oxytocin, pitressin, secretin, sincalide, terlipressin, thymopentin, thymosine α1, triptorelin, bivalirudin, carbetocin, cyclosporine, exedine, lanreotide, a luteinizing hormone-releasing hormone (LHRH), nafarelin, a parathyroid hormone, pramlintide, T-20 (enfuvirtide), thymalfasin, or ziconotide.

The present invention is also directed to providing an HA-protein conjugate, in which an HA-aldehyde derivative in which an aldehyde group is introduced into HA or a salt thereof, is bound to the N-terminus of a protein.

The HA-protein conjugate according to the present invention may be prepared according to the method as described above, but is intended to include all conjugates prepared using methods rather than the method of the present invention.

As described in the following Examples, it could be seen that the protein conjugated to the HA-aldehyde derivative in which the aldehyde group is introduced into the HA or salt thereof has a bioconjugation rate of 95% and also exhibits excellent stability, a steric structure of the protein is not affected by binding of the polymer, and the protein drug exhibits very excellent medicinal effects. Therefore, the HA-protein conjugate of the present invention may be effectively used for a drug delivery system for proteins. In particular, the HA-protein conjugate in which a ring structure is opened to conjugate with a protein while leaving a carboxyl group binding to a receptor of HA may be widely applicable to development of a therapeutic agent for treating liver diseases by maximizing the liver tissue-specific delivery characteristics of HA. Also, since liver-targeting properties of the HA may be freely controlled by controlling an aldehyde substitution rate of the HA-aldehyde derivative, the HA-protein conjugate may be effectively used to ensure persistent medicinal effects of a drug required to bypass the liver.

Advantageous Effects

The HA-protein conjugate according to the present invention includes a protein drug exhibiting a very excellent bioconjugation rate and persistent medicinal effects, and has excellent protein drug activities since the HA is specifically conjugated to the N-terminus of the protein. Also, since liver-targeting properties of the HA can be freely controlled by controlling an aldehyde substitution rate of the HA-aldehyde derivative, the HA-protein conjugate of the present invention can be effectively used as a protein drug for treating liver diseases, and also be useful in ensuring persistent medicinal effects of a protein drug required to bypass the liver. Accordingly, the HA-protein conjugate according to the present invention can be effectively used for a drug delivery system of proteins.

MODE FOR INVENTION

The advantages and features of the present invention and the method of revealing them will be explicit from the following examples described in detail. However, it is to be distinctly understood that the present invention is not limited thereto but may be otherwise variously embodied and practiced. It is obvious that the following examples are to complete the disclosure of the invention and to indicate the scope of the present invention to a skilled artisan completely, and the present invention will be defined only by the scope of the claims.

EXAMPLES

Preparative Example 1

Preparation of HA-Aldehyde Derivative

Hyaluronic acid (HA) (MW=6.4 kDa, 35 kDa, 100 kDa, 230 kDa) was dissolved in water at a concentration of 10 mg/ml, and sodium periodate was added one time per mole of an HA unit. Thereafter, the resulting mixtures were reacted for 2 hours, 6 hours, and 12 hours, respectively, under a dark condition. The reaction solution was then purified through dialysis against distilled water, and lyophilized for 3 days to obtain HA-aldehyde derivatives having different substitution rates.

Preparative Example 2

Preparation of HA-Aldehyde Derivative

Hyaluronic acid (HA) (MW=6.4 kDa, 35 kDa, 100 kDa, 230 kDa) was dissolved in water at a concentration of 5 mg/ml, and adipic acid dihydrazide (ADH) was added at 20 molar excess of an HA unit. Thereafter, the resulting mixture solutions were adjusted to pH 4.8 using HCl, and stirred for 30 minutes. N-(3-dimethylaminopropyl)-N'-ethylcarbodiimide (EDC) hydrochloride (Mw=191.71) was added to the mixture solutions at four molar excess of an HA unit. Then, the resulting mixture solutions were reacted for 3 minutes and 2 hours, respectively, while maintaining a pH value at pH 4.8. Subsequently, the reaction solutions were purified through dialysis against distilled water, and lyophilized for 3 days to obtain HA-ADH derivatives having different substitution rates. Each of the prepared HA-ADH derivatives was dissolved in a sodium acetate buffer solution (pH 5.2) at a concentration of 10 mg/ml, and glutaraldehyde was then added at 10 molar excess of the added ADH. The resulting mixture was then reacted for 24 hours. Subsequently, the reaction solution was then purified through dialysis against distilled water, and lyophilized for 3 days to obtain HA-ADH-aldehyde derivatives having different substitution rates.

Experimental Example 1

Analysis of Substitution Rate of HA-Aldehyde Derivative

The HA-aldehyde derivative prepared in Preparative Example 1 was dissolved in a sodium acetate buffer solution (pH 5.2) at a concentration of 5 mg/ml, and tetrabutyl carbazate (TBC) and sodium cyanoborohydride (NaBH$_3$CN) were added at five molar excess of an HA unit. The resulting mixture solution was then reacted for 24 hours. The reaction solution was dialyzed against distilled water, and then lyophilized for 3 days to analyze a substitution rate of aldehyde using $^1$H-NMR (DPX300, Bruker, Germany).

Figure 1:
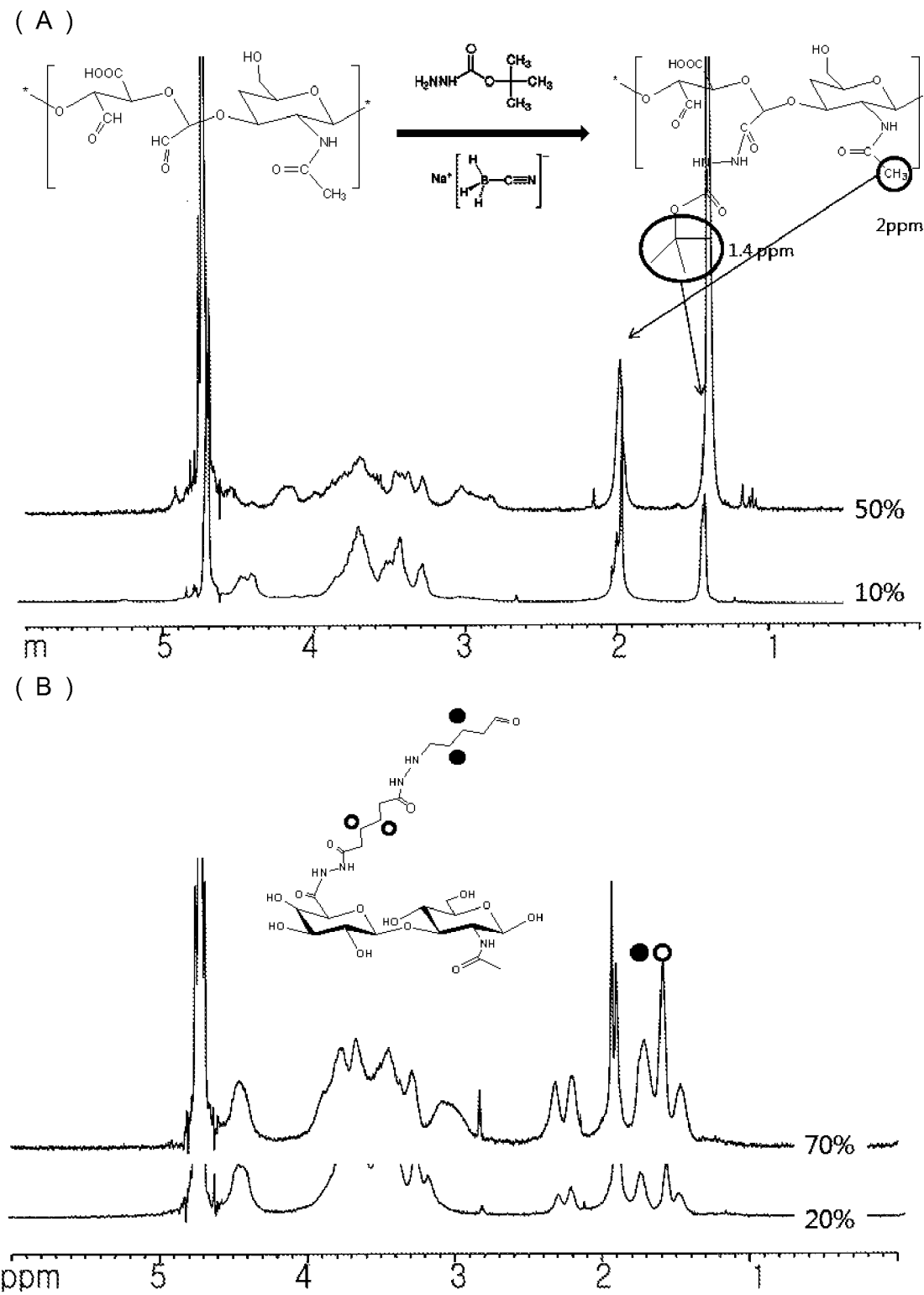
FIG. 1A shows the $^1$H-NMR results of an HA-aldehyde-TBC derivative prepared by a method described in Preparative Example 1 of the present invention according to a substitution rate.
FIG. 1B shows the $^1$H-NMR results of an HA-aldehyde-TBC derivative prepared by a method described in Preparative Example 2 of the present invention according to a substitution rate.

As a result, it was revealed that three methyl peaks of TBC indicating 9 hydrogen atoms were observed at δ=1.2 to 1.4 ppm, in addition to peaks of HA on the $^1$H-NMR spectra of the HA-TBC derivative prepared in Preparative Example 1, as shown in FIG. 1. For quantitative analysis, the methyl resonance of acetamido moiety of HA at δ=1.85 to 1.95 ppm was defined as an internal standard. The substitution rate of the HA-aldehyde derivative prepared in Preparative Example 1 was calculated by comparing a peak area at δ=1.85 to 1.95 ppm with a peak area at δ=1.2 to 1.4 ppm. From these $^1$H-NMR analysis results, the substitution rate of the HA-aldehyde derivative was calculated. As a result, it was revealed that the HA-aldehyde derivatives whose substitution rate was controlled to 10 to 50% were obtained by controlling the reaction time with the sodium periodate (10% for 2 hours, 25% for 12 hours, and 45% for 24 hours).

Experimental Example 2

Analysis of Substitution Rate of HA-Aldehyde Derivative

The HA-aldehyde derivative prepared in Preparative Example 2 was dissolved in a sodium acetate buffer solution (pH 5.2) at a concentration of 5 mg/ml, and TBC and NaBH$_3$CN were added at five molar excess of an HA unit. The resulting mixture solution was then reacted for 24 hours. The reaction solution was dialyzed against distilled water, and then lyophilized for 3 days to analyze a substitution rate of aldehyde using $^1$H-NMR (DPX300, Bruker, Germany). As a result, it was revealed that three methyl peaks of TBC indicating 9 hydrogen atoms were observed at δ=1.2 to 1.4 ppm, in addition to peaks of HA on the $^1$H-NMR spectra of the HA-TBC derivative prepared in Preparative Example 2, as shown in FIG. 1B. For quantitative analysis, the methyl resonance of acetamido moiety of HA at δ=1.85 to 1.95 ppm was defined as an internal standard. The substitution rate of the HA-aldehyde derivative prepared in Preparative Example 2 was calculated by comparing a peak area at δ=1.85 to 1.95 ppm with a peak area at δ=1.2 to 1.4 ppm. From these $^1$H-NMR analysis results, the substitution rate of the HA-aldehyde derivative was calculated. As a result, it was revealed that the HA-aldehyde derivatives whose aldehyde substitution rate was controlled to 20 to 70% were obtained according to the substitution rate of the introduced ADH.

Preparative Example 3

Preparation of Conjugate Between HA-Aldehyde Derivative and Protein

The HA-aldehyde derivative prepared in Preparative Example 1 was dissolved in an acetate buffer solution (pH 6) at a concentration of 10 mg/ml, and IFNα in an aqueous solution phase was added so that the number of IFNα molecules per single HA chain was varied among 1, 4, 6, and 9. NaBH$_3$CN was added at five molar excess of the aldehyde according to the substitution rate of the HA-aldehyde derivative. The resulting mixture solution was reacted for 24 hours to obtain an HA-IFNα conjugate.

To block the residual aldehyde remaining unreacted in the HA-IFNα conjugate, ethyl carbazate was added at five molar excess of the aldehyde, and reacted for another 24 hours, or amino ethanol was added at five molar excess of the aldehyde, and reacted for another 3 hours at pH 8. The resulting reaction solution was dialyzed against phosphate buffered saline (PBS, pH 7.4), and then stored at −70° C. In all the following Experimental Examples 3, 5, 6, 7, 8, 9, 10 and 11, the HA-IFNα conjugate in which 6 IFNα molecules were conjugated per single HA chain was used.

Experimental Example 3

GPC Analysis of HA-IFNα Conjugate

Formation of the HA-IFNα conjugate was confirmed through GPC analysis of the HA-IFNα conjugate prepared in Preparative Example 3.

The GPC analysis of the HA-IFNα conjugate was performed using high performance liquid chromatography (HPLC). The analysis conditions were as described below.

GPC Analysis Conditions

Pump: Waters 1525 binary HPLC pump

Absorbance detector: Waters 2487 dual λ absorbance detector

Sampler: Waters 717 plus auto-sampler

Column: Waters Ultrahydrogel 500+Waters Ultrahydrogel 250

Mobile phase: PBS (pH 7.4) at a flow rate of 0.5 mL/min.

Measurement wavelength: dual detection at 210 nm and 280 nm.

Figure 2:
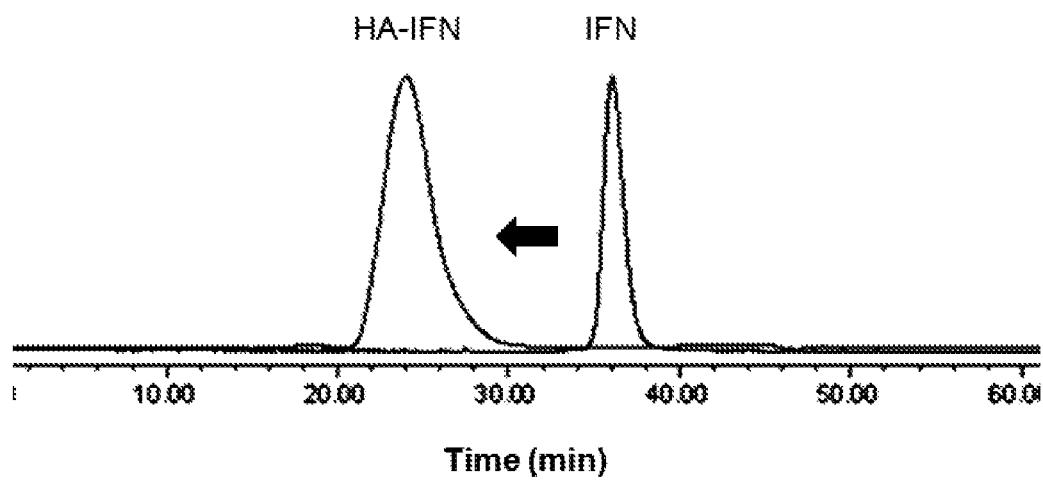
FIG. 2 shows the gel permeation chromatography (GPC) results of an HA-interferon alpha (IFNα) conjugate and a protein prepared by the method described in Preparative Examples of the present invention.

As seen from FIG. 2, the analysis results revealed that a peak was observed at a time point of 22 minutes which was a retention time of the high molecular weight hyaluronic acid when measured at a wavelength of 280 nm, indicating that the IFNα was conjugated with HA.

Experimental Example 4

Quantitative Analysis of HA-IFNα Conjugate

A content of the IFNα in the HA-IFNα conjugate prepared in Preparative Example 3 was calculated by measuring an area under the peaks on GPC. First, an IFNα stock solution was prepared at a concentration of 1 mg/mL, and then diluted with distilled water to prepare an IFNα standard solution. The IFNα standard solution was analyzed under the GPC analysis conditions described in Experimental Example 3 to plot a standard curve of an area under the GPC peaks according to the IFNα concentration. A content of the protein was calculated by applying the area under the GPC peaks, which was obtained by analyzing the HA-IFNα conjugate prepared in Preparative Example 3 under the same conditions, to the standard curve.

Figure 3:
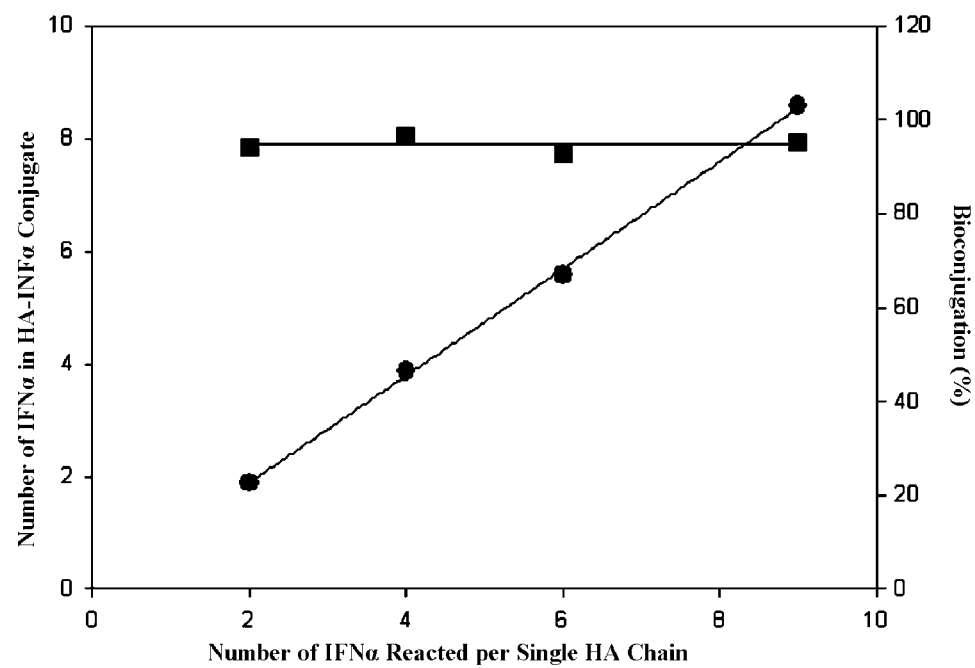
FIG. 3 shows the bioconjugation efficiencies according to the number of interferon molecules and the number of protein molecules included in one HA chain of the HA-IFNα conjugate.

As seen from FIG. 3, the analysis results revealed that the content of the protein in the HA-IFNα conjugate prepared in Preparative Example 3 increased as the number of molecules of the protein which reacted per molecule of HA in the feed increased. It was confirmed that, when the number of molecules of the protein which reacted per molecule of HA was varied among 1, 4, 6, and 9, the average number of molecules of the protein which reacted per molecule of HA was controlled to 1, 4, 6, and 9, respectively. The bioconjugation efficiency (%) was proven to be equal to or greater than 95% regardless of the number of molecules.

Experimental Example 5

CD Analysis of HA-IFNα Conjugate

Based on the concentration of IFNα, the CD analyses were performed using the (0.25 mg/ml) IFNα solution and the solution of the HA-IFNα conjugate prepared in Preparative Example 3. The analysis conditions were as described below.

CD Analysis Conditions

UV spectrophotometer: JASCO J-715

Measurement conditions: 25° C., 200 to 250 nm, $N_2$ atmosphere

Quartz cuvette: path length of 2 mm

Raw data: intervals of 0.2 mm with a response time of one second.

Figure 4:
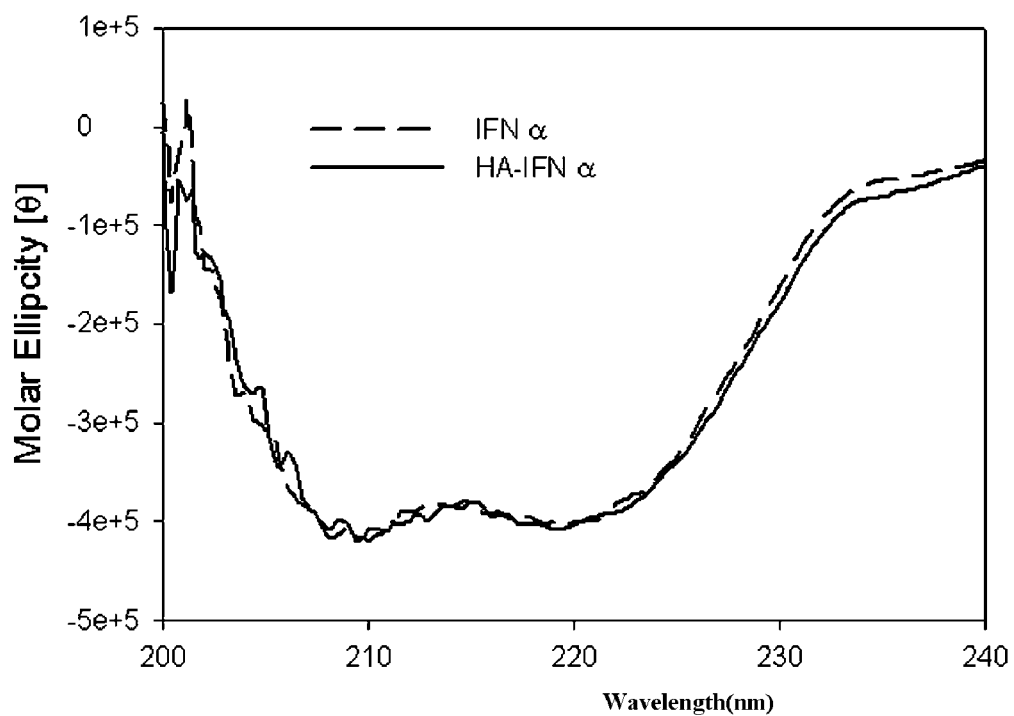
FIG. 4 shows the comparison of the circular dichroism (CD) assay results of IFNα and the HA-IFNα conjugate.

As seen from FIG. 4, the analysis results revealed that the spectra of IFNα were well matched with the CD peaks of the HA-IFNα conjugate, indicating that a secondary structure of IFNα was maintained in a state in which IFNα was conjugated with HA.

Experimental Example 6

Analysis of Activities of HA-IFNα Conjugate

The activities of the HA-IFNα conjugate were analyzed through the ratio between ELISA/Bradford assays. First, a 1 mg/ml IFNα stock solution was prepared, and diluted to prepare an IFNα standard solution. The absorbance was measured according to the increasing concentration using a Bradford assay to plot a standard curve. The HA-IFNα conjugate prepared in Preparative Example 3 and the IFNα were diluted, and measured for absorbance under the same conditions using a Bradford assay, and the measured absorbance was applied to the standard curve to calculate a content of IFNα. Also, the sample used in the Bradford assay and the standard solution was diluted 10,000 times to calculate a content of IFNα having activities through ELISA. Thereafter, the activities of the HA-IFNα conjugate were analyzed through the ratio between the ELISA/Bradford assays.

Figure 5:
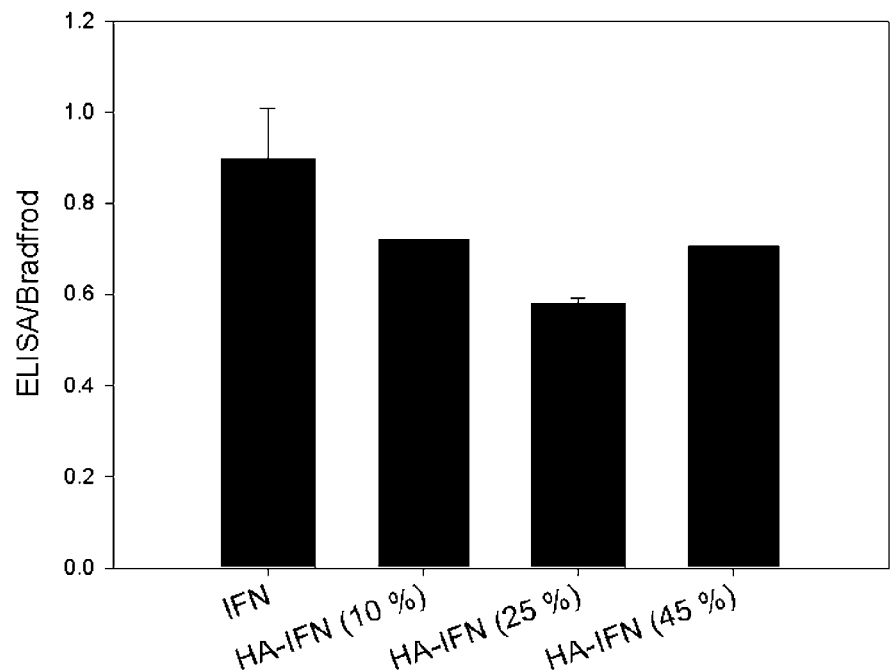
FIG. 5 shows the analysis results of biological activities of the IFNα and the HA-IFNα conjugate prepared in one preparative example of the present invention through an ELISA assay.

As seen from FIG. 5, the analysis results revealed that the HA-IFNα conjugate had an activity ratio of 70% or more, as measured through the ELISA/Bradford assays. The Bradford assay is an analytic method of measuring a content of lysine in a protein, and the ELISA is an analytic method of quantifying a content of IFNα using binding of IFNα to an antibody. From the activity ratio, it could be seen that 70% or more amino acids present in the protein had activities.

Experimental Example 7

Activity Test of HA-IFNα Conjugate

The activities of IFNα were tested using human B-lymphoblastoid cells (Daudi cells) which were reported to poorly grow in the presence of IFNα.

First, a 1 mg/ml IFNα stock solution was prepared, and then diluted to prepare an IFNα standard solution. The absorbance was measured according to the increasing concentration using a Bradford assay to plot a standard curve. The HA-IFNα conjugate prepared in Preparative Example 3 and the IFNα were diluted, and measured for absorbance under the same conditions using a Bradford assay, and the measured absorbance was then applied to the standard curve to calculate a content of IFNα. Daudi cells were incubated for 5 days in media including the standard solution and the diluted sample, respectively, and growth rates of the Daudi cells were confirmed through an MTS assay.

Figure 6:
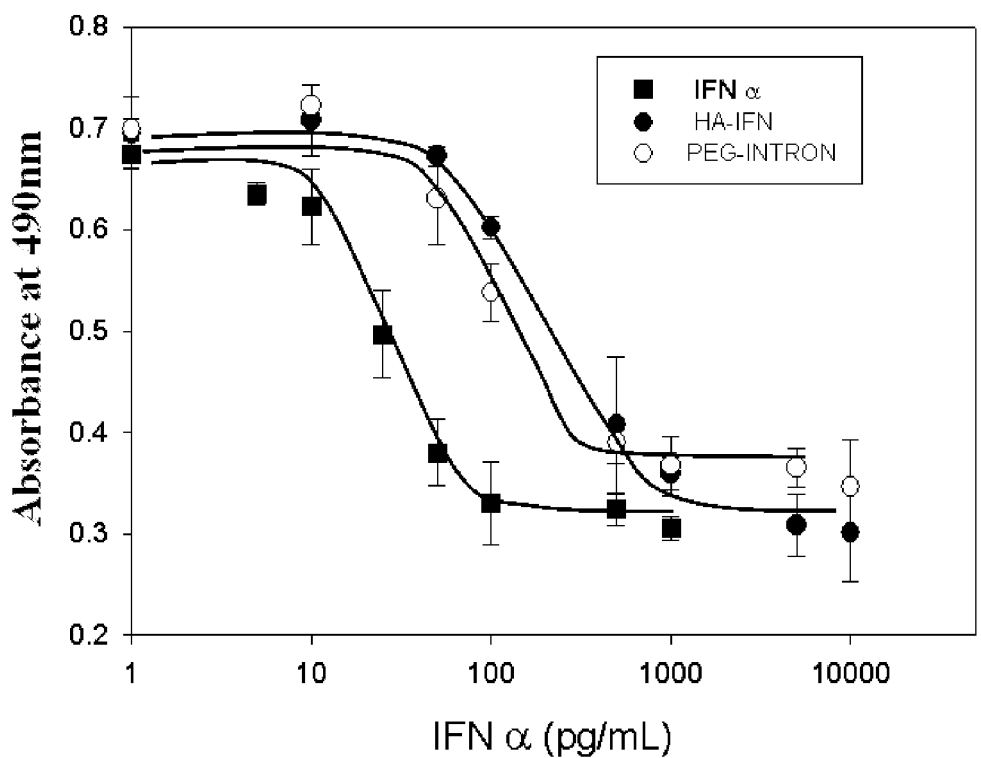
FIG. 6 shows the analysis results of biological activities of the IFNα and the HA-IFNα conjugate prepared in one preparative example of the present invention through an antiproliferation assay using Daudi cells.

As seen from FIG. 6, the analysis results revealed that the activities of the HA-IFNα conjugate were lower than those of the IFNα standard solution, but were similar to those of commercially available PEGASYS.

Experimental Example 8

Analysis of Anti-Cancer Effects of HA-IFNα Conjugate

HepG2 cells which were liver cancer cells were treated with the HA-IFNα conjugate, and viability of the HepG2 cells was analyzed through an MTT assay to test anti-cancer effects of the HA-IFNα conjugate.

First, a 1 mg/ml IFNα stock solution was prepared, and then diluted to prepare an IFNα standard solution. The absorbance was measured according to the increasing concentration using a Bradford assay to plot a standard curve. The HA-IFNα conjugate prepared in Preparative Example 3 and the IFNα were diluted, and measured for absorbance under the same conditions using a Bradford assay, and the measured absorbance was then applied to the standard curve to calculate a content of IFNα. HepG2 cells were incubated for 3 days in media including the standard solution and the diluted sample, respectively, and viabilities of the HepG2 cells were confirmed through an MTT assay.

Figure 7:
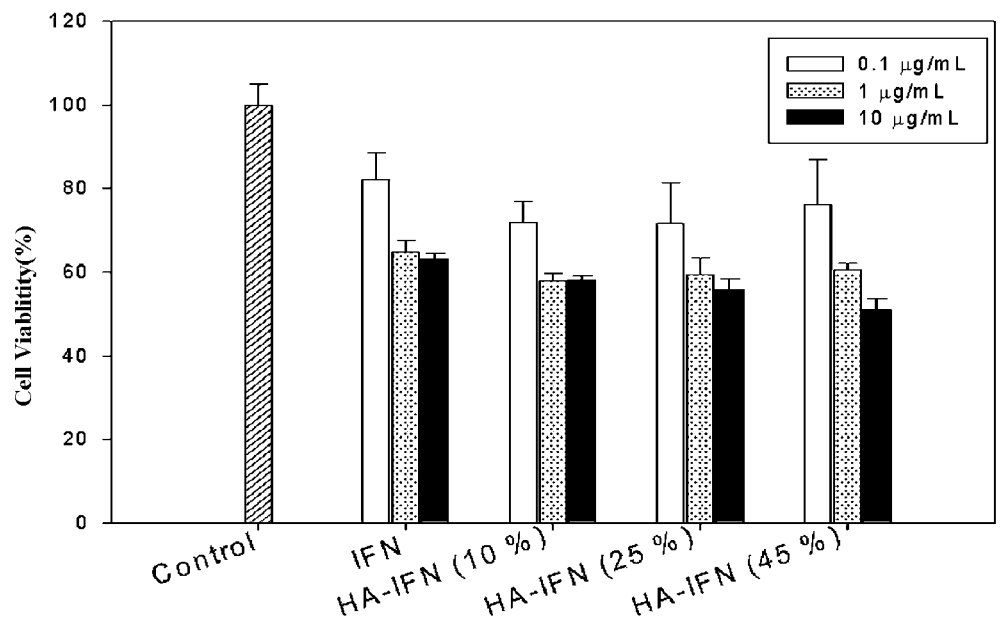
FIG. 7 shows the anti-cancer therapeutic effects of the IFNα and the HA-IFNα conjugate prepared in one preparative example of the present invention through an antiproliferation assay using HepG2 hepatoma cells.

As seen from FIG. 7, the analysis results revealed that the HA-IFNα conjugate had anti-cancer effects similar to the IFNα standard solution.

Experimental Example 9

Half-Life Analysis (In Vitro) of HA-IFNα Conjugate

The IFNα and the HA-IFNα conjugate (10%/6) (HA-IFNα conjugate having an aldehyde substitution rate of 10% and including 6 IFNα molecules conjugated per single HA chain) were used for samples for analysis to analyze the half-lives of the IFNα and the HA-IFNα conjugate.

Each of the samples was dissolved in human serum so that IFNα was present at the same concentration of 1 mg/mL, and incubated at 37° C. for 120 hours. At a predetermined time point, the resulting mixture was sampled, and then diluted 1,000 times and frozen to prevent an effect of human serum on the samples. Biological activities of each sample were measured using an IFNα ELISA kit and an MTS assay using Daudi cells.

Figure 8:
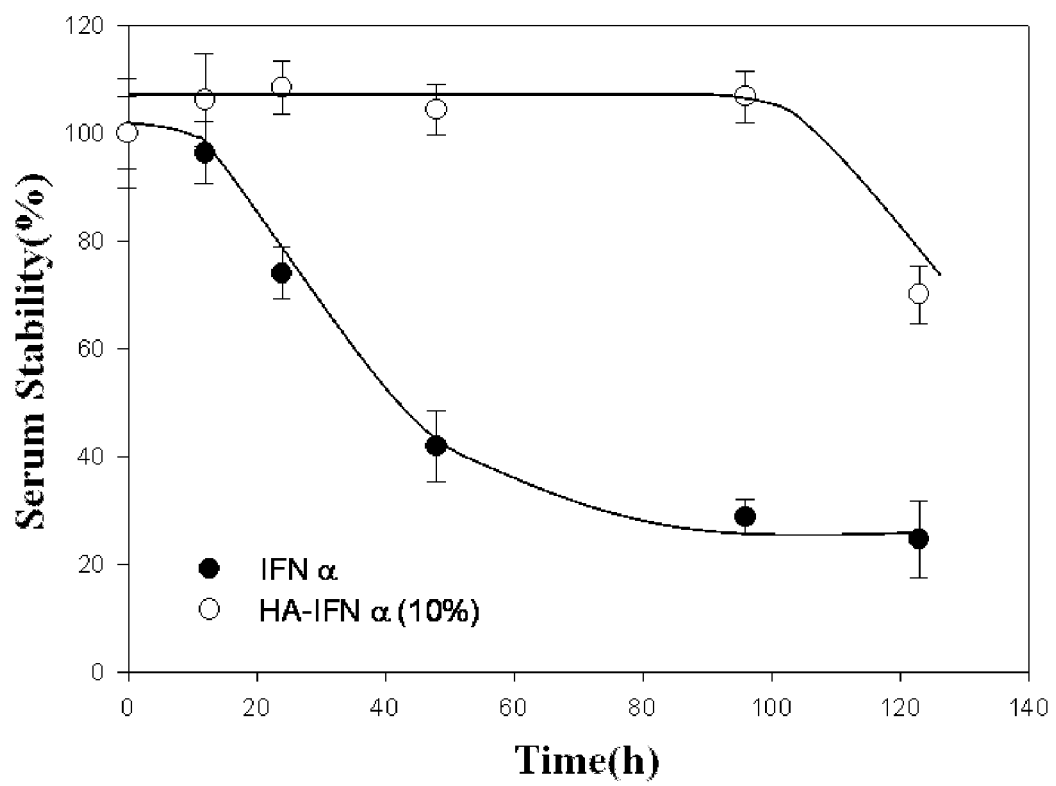
FIG. 8 shows the comparison of stabilities of the IFNα and the HA-IFNα conjugate prepared in one preparative example of the present invention in human serum.

As seen from FIG. 8, the analysis results revealed that IFNα was rapidly decomposed within 24 hours. However, the half-life of the HA-IFN conjugate (10%/6) extended to 120 hours or more, the half-life of which was approximately five times longer than that of the IFNα.

Experimental Example 10

Figure 9:
FIG. 9 shows the real-time bioimaging results of the IFNα (A) and the HA-IFNα conjugate (B) prepared in one preparative example of the present invention, both of which are labeled with a near infrared ray fluorescence (NIRF) dye after tail vein injection.
Figure 9:
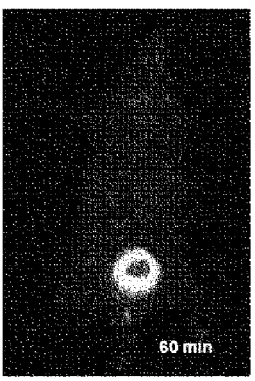
Figure 9:
Figure 9:
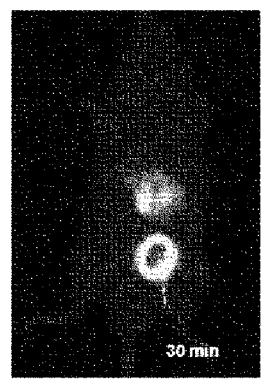
Figure 9:
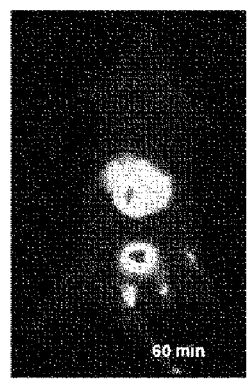

In Vivo Imaging of HA-IFNα Conjugate and Analysis (In Vivo) of Pharmacokinetic (PK) Characteristics To determine systemic distribution of the HA-IFNα conjugate, in vivo imaging was performed on the HA-IFNα conjugate. The IFNα and the HA-IFNα conjugate (10%/6) were labeled with a near infrared ray fluorescence (NIRF) dye, and injected into veins of Balb/c mice. The mice were anesthetized 30 minutes and an hour after the injection, and the fluorescence was captured using a luminescent image analyzer. As seen from FIG. 9, the NIRF dye-labeled HA-IFNα conjugate was delivered into the liver in a target-specific manner, but the NIRF dye-IFNα bonds were uniformly distributed, and then eliminated due to renal clearance showing the fluorescence in the bladder. The results were well matched with real-time bioimaging results in previously reported theses disclosing the target-specific delivery of the HA derivatives into the liver using QDots, and supported the feasibility of the HA-IFNα conjugate for treatment of liver diseases.

Meanwhile, each of PBS, IFNα, and the HA-IFNα conjugate (degrees of substitution of 10%, 25%, and 45%, respectively) was administered through veins of SD rat tails, and blood was taken from the veins of SD rat tails at a predetermined time point. Then, a blood concentration of each sample was measured using an IFNα ELISA kit.

Figure 10:
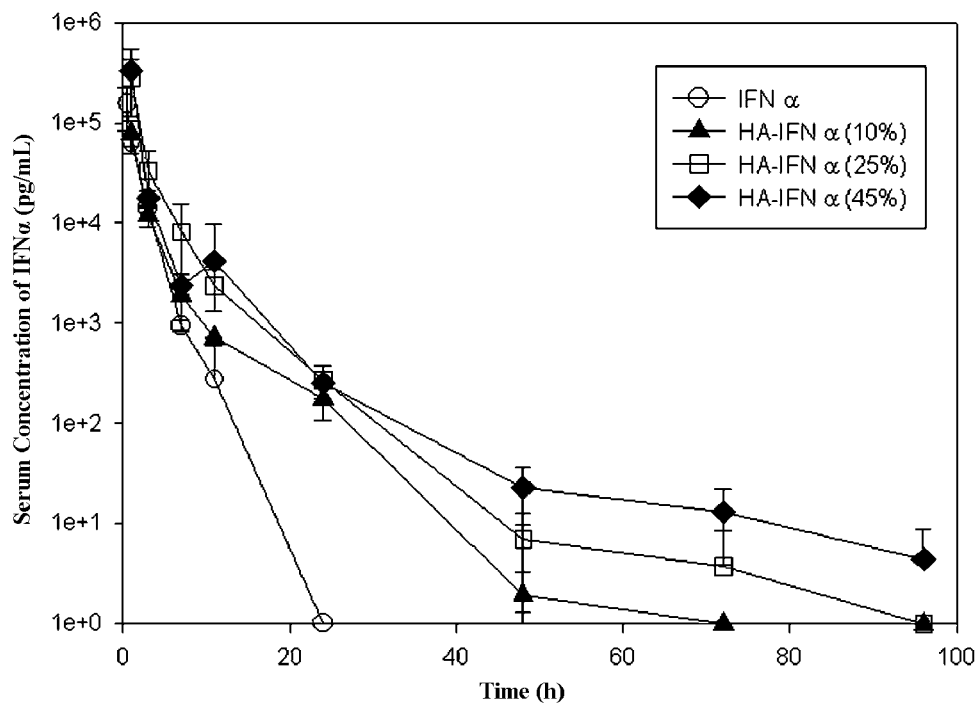
FIG. 10 shows the pharmacokinetic analysis results of the HA-IFNα conjugate prepared in one preparative example of the present invention.

As seen from FIG. 10, the analysis results revealed that the blood IFNα concentration dropped to the baseline within 24 hours, but the blood concentration of the HA-IFNα conjugate (45%/6) had still not dropped to the baseline by a time point of day 4.

Experimental Example 11

Analysis (In Vivo) of Anti-Viral Characteristics of HA-IFNα Conjugate

2'-5'-oligoadenylate synthetase 1 (OAS1) was an anti-viral protein whose expression was induced by IFNα and which took part in an innate immune response against viral infections. OAS1 was an enzyme associated with a reaction of synthesizing 2'-5'-oligoadenylate which activates RNase L for degradation of double-stranded RNA and inhibition of viral replication. The anti-viral activities of IFNα were highly associated with an expression level of OAS1.

Each of PBS, IFNα, the HA-IFNα conjugate (10%/6), and the HA-IFNα conjugate (45%/6) was administered through veins of Balb/c mouse tails (injected dose of 0.2 mg/kg based on IFNα). 24 hours after the injection, the livers of the mice were extracted, and a level of OAS1 was quantified using a Western blotting assay.

Figure 11:
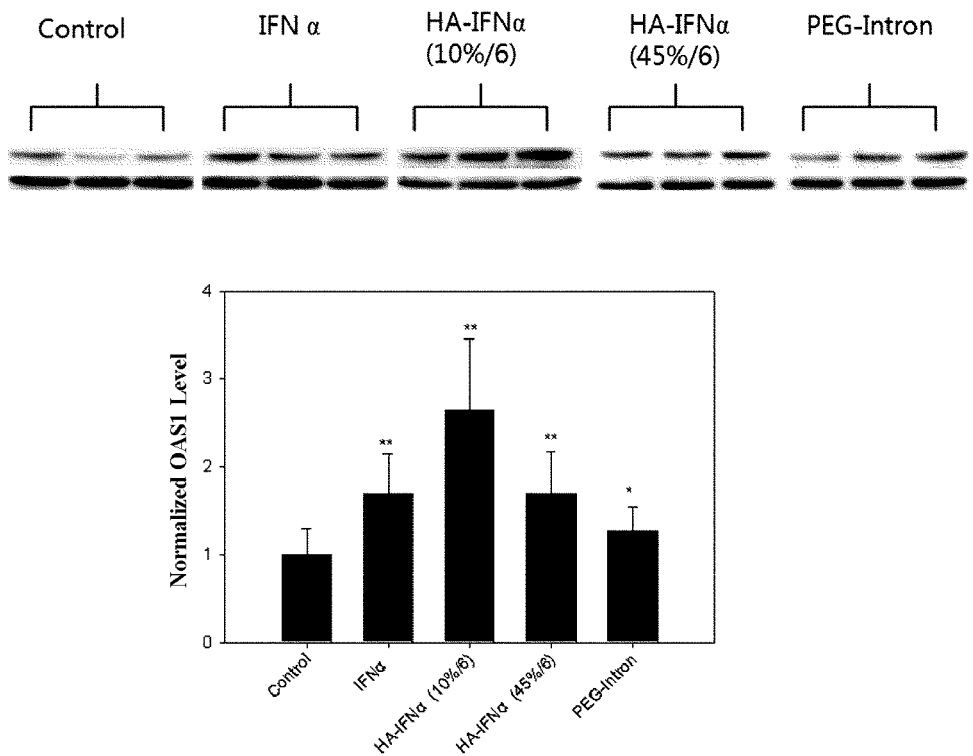
FIG. 11 shows the anti-viral activity analysis results of the HA-IFNα conjugate prepared in one preparative example of the present invention in the livers of rats.

As seen from FIG. 11, it could be seen that the HA-IFNα conjugate having a lower substitution rate than IFNα was easily delivered into the liver and had a long body retention time, and thus the OAS1 playing an anti-viral role in the liver was observed at an increased level. Also, the HA-IFNα conjugate having a higher substitution rate exhibited poorer delivery characteristics into the liver, compared with the HA-IFNα conjugate having a lower substitution rate, but had a higher OAS1 level than the IFNα due to an increase in body retention time.

What is claimed is:

1. A method for preparing a hyaluronic acid (HA)-protein conjugate, comprising:
allowing an HA-aldehyde derivative in which at least one aldehyde group is introduced into the glucuronic acid backbone of hyaluronic acid or a salt thereof to react with an N-terminus of a protein to thereby obtain the HA-protein conjugate, wherein the protein is selected from the group consisting of interferon alpha (IFNα), interferon beta (IFNβ), interferon gamma (IFNγ), and a tumor necrosis factor (TNF), and wherein the HA-aldehyde derivative has an aldehyde substitution rate of 5% or more and less than 30%, such that the HA-protein conjugate has a longer half-life than the protein.

2. The method of claim 1, wherein the HA-aldehyde derivative has at least one aldehyde group at the terminus of a ring which is opened at the glucuronic acid backbone of the HA or salt thereof.

3. The method of claim 2, wherein the HA-aldehyde derivative is obtained by allowing the HA or salt thereof to react with an oxidizing agent.

4. The method of claim 3, wherein the oxidizing agent is able to ring-open the glucuronic acid backbone of the HA or salt thereof to form at least one aldehyde group.

5. The method of claim 4, wherein the oxidizing agent is a periodate.

6. The method of claim 3, wherein an aldehyde substitution rate of the HA or salt thereof is controlled by controlling a reaction time between the HA or salt thereof and the oxidizing agent.

7. The method of claim 1, wherein the HA-aldehyde derivative is a derivative in which an aldehyde group is introduced at a carboxyl position present at the glucuronic acid backbone of the HA or salt thereof.

8. The method of claim 7, wherein the HA-aldehyde derivative is obtained by allowing a carboxyl group of the hyaluronic acid or a derivative thereof to react with a molecule containing a diamine or dihydrazide group, followed by allowing a derivative of the molecule to react with another molecule containing a dialdehyde group.

9. The method of claim 1, wherein the reaction of the HA-aldehyde derivative with the N-terminus of the protein is performed in the presence of a reagent serving to induce reductive amination.

10. The method of claim 9, wherein the reagent serving to induce the reductive amination is sodium cyanoborohydride (NaBH$_3$CN), or sodium triacetoxyborohydride (NaBH(OCH$_3$)$_3$).

11. The method of claim 1, wherein the reaction of the HA-aldehyde derivative with the N-terminus of the protein is performed in a buffer solution with pH 5 to 7.

12. The method of claim 1, wherein the reaction of the HA-aldehyde derivative with the N-terminus of the protein is performed in the buffer solution with pH 5.5 to 6.5.

13. The method of claim 1, further comprising:
 blocking an unreacted aldehyde group, which does not react with the N-terminus of the protein in the HA-aldehyde derivative, with a protecting group.

14. The method of claim 1, wherein the HA or salt thereof has a molecular weight of 10,000 to 3,000,000 daltons (Da).

15. The method of claim 1, wherein the number of molecules of the protein conjugated per one molecule of the HA-aldehyde derivative is in a range of 1 to 20.

16. A hyaluronic acid (HA)-protein conjugate in which an HA-aldehyde derivative is conjugated to an N-terminus of a protein selected from the group consisting of interferon alpha (IFNα), interferon beta (IFNβ), interferon gamma (IFNγ), and a tumor necrosis factor (TNF), wherein the HA-aldehyde derivative comprises at least one aldehyde group introduced into the glucuronic acid backbone of hyaluronic acid or a salt thereof, and wherein the HA-aldehyde derivative has an aldehyde substitution rate of 5% or more and less than 30% such that the HA-protein conjugate has a longer half-life than the protein.

17. The HA-protein conjugate of claim 16, wherein the HA or salt thereof has a molecular weight of 10,000 to 3,000,000 Da.

18. The HA-protein conjugate of claim 16, wherein the number of molecules of the protein conjugated per one molecule of the HA-aldehyde derivative is in a range of 1 to 20.

19. The HA-protein conjugate of claim 16, wherein the HA-protein conjugate is used to treat a liver disease.

20. The HA-protein conjugate of claim 16, wherein the protein is IFNα.

* * * * *